(12) United States Patent
Benditt et al.

(10) Patent No.: US 7,097,618 B1
(45) Date of Patent: Aug. 29, 2006

(54) DEVICES AND METHODS FOR DETECTING AND TREATING INADEQUATE TISSUE PERFUSION

(75) Inventors: David G. Benditt, Edina, MN (US); Brian P. Brockway, Shoreview, MN (US); Richard R. Wilson, Arden Hills, MN (US)

(73) Assignee: Transoma Medical, Inc., St. Paul, MN (US)

( * ) Notice: Subject to any disclaimer, the term of this patent is extended or adjusted under 35 U.S.C. 154(b) by 200 days.

(21) Appl. No.: 10/797,584

(22) Filed: Mar. 9, 2004

Related U.S. Application Data

(60) Provisional application No. 60/454,951, filed on Mar. 12, 2003.

(51) Int. Cl.
*A61B 5/05* (2006.01)
*A61B 5/00* (2006.01)
(52) U.S. Cl. ..................... 600/363; 600/300
(58) Field of Classification Search .............. 600/323, 600/363; 607/23
See application file for complete search history.

(56) References Cited

U.S. PATENT DOCUMENTS

| | | | |
|---|---|---|---|
| 4,899,751 A * | 2/1990 | Cohen | 607/23 |
| 5,487,760 A | 1/1996 | Villafana | |
| 5,913,879 A | 6/1999 | Ferek-Petri et al. | |
| 6,033,366 A * | 3/2000 | Brockway et al. | 600/486 |
| 6,351,670 B1 | 2/2002 | Kroll | |
| 6,491,639 B1 | 12/2002 | Turcott | |
| 6,510,342 B1 * | 1/2003 | Park et al. | 607/15 |
| 6,575,914 B1 * | 6/2003 | Rock et al. | 600/500 |
| 6,616,624 B1 * | 9/2003 | Kieval | 604/8 |
| 6,625,492 B1 | 9/2003 | Florio et al. | |
| 6,647,295 B1 | 11/2003 | Florio et al. | |
| 6,662,047 B1 | 12/2003 | Sorensen et al. | |
| 2003/0229380 A1 * | 12/2003 | Adams et al. | 607/9 |

FOREIGN PATENT DOCUMENTS

WO  WO 98/51212  * 11/1998

* cited by examiner

*Primary Examiner*—Robert L. Nasser
*Assistant Examiner*—Patricia Mallari
(74) *Attorney, Agent, or Firm*—Townsend and Townsend and Crew LLP

(57) ABSTRACT

Devices and methods for detecting inadequate tissue perfusion by measuring a parameter other than heart rate such as vascular blood pressure, intracardiac blood pressure, vascular blood flow or tissue perfusion, in addition to or as a substitute for heart rate. Such devices and methods improve the accuracy of determining when and to what degree therapy should be administered to treat inadequate tissue perfusion, such as pre-syncope, syncope, or orthostatic hypotension, particularly in the absence of abnormal cardiac function.

12 Claims, 6 Drawing Sheets

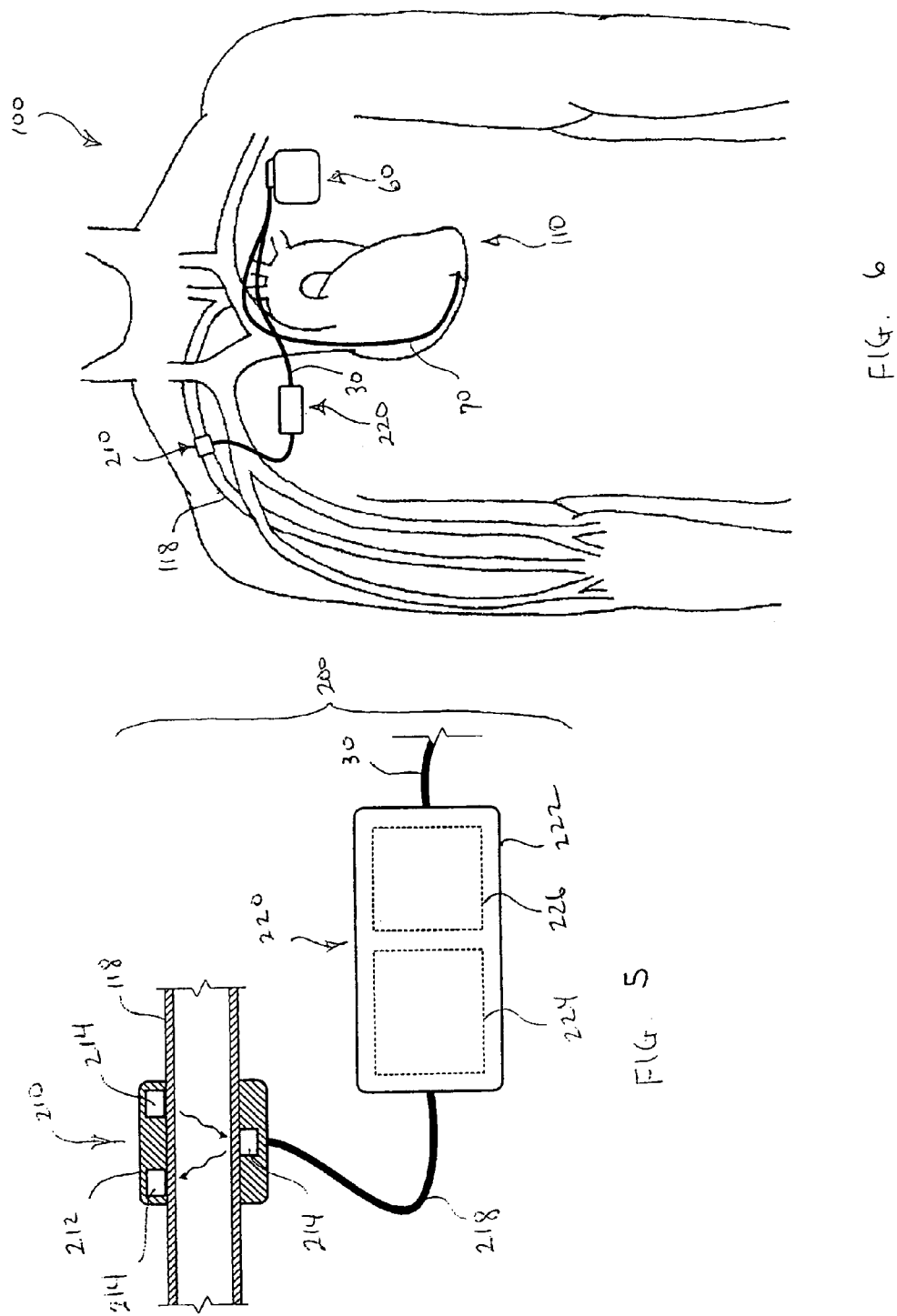

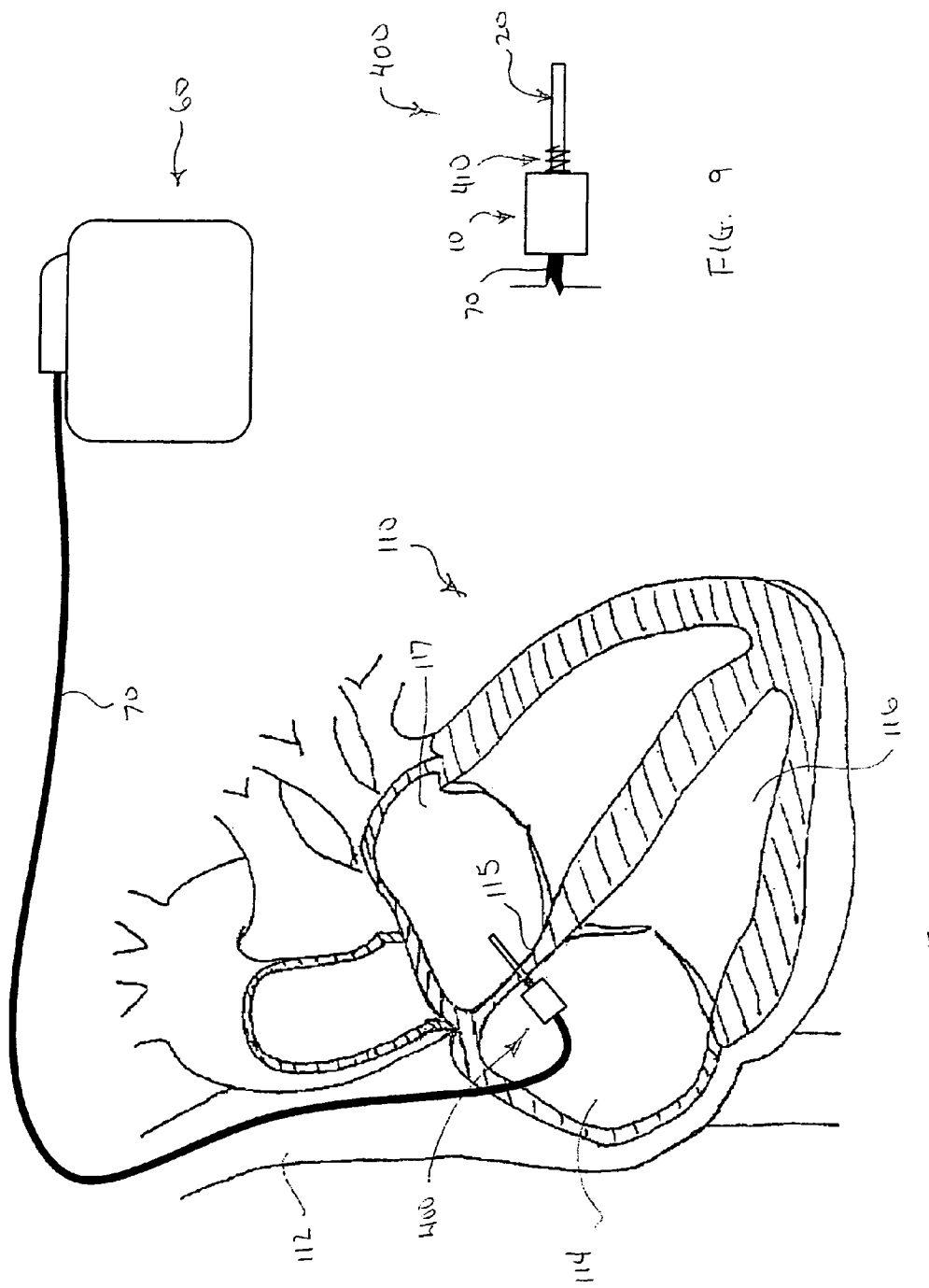

DEVICES AND METHODS FOR DETECTING AND TREATING INADEQUATE TISSUE PERFUSION

CROSS-REFERENCES TO RELATED APPLICATIONS

The present application claims benefit under 35 U.S.C. § 119(e) of U.S. Provisional Application No. 60/454,951, filed Mar. 12, 2003, which is incorporated by reference.

BACKGROUND OF THE INVENTION

Field of the Invention

The present invention generally relates to devices used in the treatment of inadequate tissue perfusion. In particular, the present invention relates to devices and methods for improving the detection and analysis of episodes of inadequate tissue perfusion to enable more effective therapy.

In certain disease states, including, but not limited to, pre-syncope, syncope, and orthostatic hypotension, the cardiovascular system does not adequately respond to decreases in intravascular pressure. Low intravascular pressure results in under-perfusion of body tissues, particularly upper body tissues such as the brain. In a significant number of these cases, a demonstrable cardiac arrhythmia is not present but the integrated cardiovascular response is inadequate to correct the hypotensive episode.

Unfortunately, devices used to treat patients with this malady, such as pacemakers or infusion pumps, often do not perform adequately. These devices conventionally rely on ECG and/or electrogram as a means to effect the control of the delivery of a therapy. For example, when the patient's heart rate, as detected from ECG and/or electrogram, falls below a predetermined level, a pacemaker delivers electrical stimuli to the heart to increase the heart rate. The efficacy of this approach is limited to pathophysiologic circumstances in which reductions in tissue perfusion occur at the same time as and to the same degree as reductions in heart rate. If the pathologic drop in tissue perfusion occurs in the presence of a normal cardiac rhythm and rate, the use of ECG and/or electrogram is inadequate as means of determining when and to what degree therapy should be delivered.

BRIEF SUMMARY OF THE INVENTION

To address this problem, the present invention provides, in exemplary non-limiting embodiments, devices and methods for detecting inadequate tissue perfusion by measuring a parameter other than heart rate. For example, by measuring peripheral vascular blood pressure, intracardiac blood pressure, vascular blood flow or tissue perfusion in addition to or as a substitute for heart rate as measured by ECG or electrogram, the present invention improves the accuracy of determining when and to what degree therapy should be administered to treat inadequate tissue perfusion. The present invention also provides devices and methods to detect in real time any discrepancy between hemodynamic status and cardiac response, and to then direct interventions appropriately.

BRIEF DESCRIPTION OF THE DRAWINGS

FIG. 5 is a schematic illustration of a flow sensing device that may be used in place of the pressure sensing device.

FIG. 6 is a schematic illustration of a flow sensing device and a pacemaker shown implanted in a patient.

FIG. 9 is a schematic illustration of a system including an implantable pacemaker and an implantable pressure sensing device.

FIG. 10 is a schematic illustration of a pressure sensing device with an anchoring electrode shown implanted across a patient's atrial septal wall.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Generic Description of Methods

Figure 1:
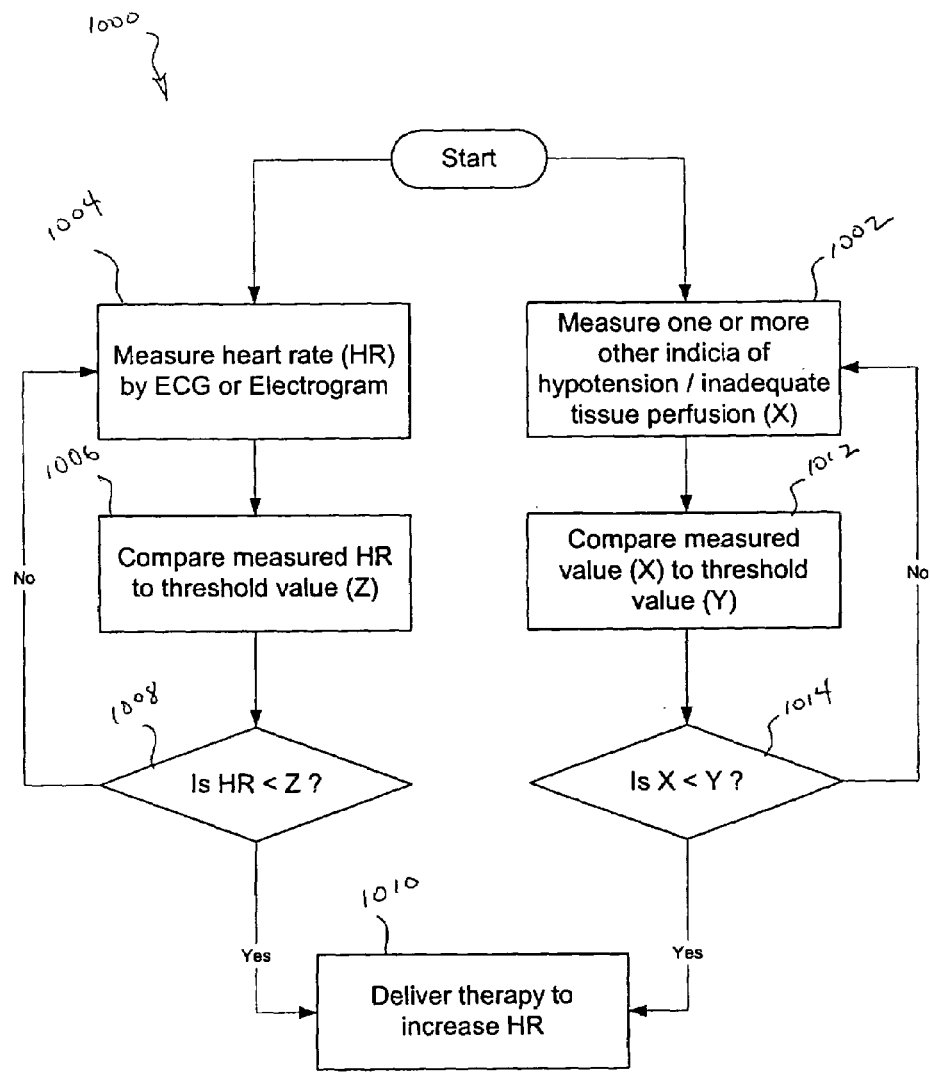
FIG. 1 is a schematic flow chart illustrating the basic steps involved in a method of detecting and providing therapy for inadequate tissue perfusion, according to an exemplary non-limiting embodiment of the present invention.

With reference to FIG. 1, a method 1000 of detecting and providing therapy for inadequate tissue perfusion is shown schematically. Those skilled in the art will recognize that this method 1000 is illustrative of general concepts according to an exemplary non-limiting embodiment of the present invention for detecting and providing therapy for conditions of inadequate tissue perfusion such as pre-syncope, syncope, and orthostatic hypotension.

In this illustrative method 1000, one or more indicia (X) of inadequate tissue perfusion are measured 1002 to supplement or replace heart rate (HR) measurements 1004 normally taken by ECG or electrogram. The ECG or electrogram measurement 1004 may be obtained using conventional techniques such as utilizing feedback electrodes disposed on a pacemaker implanted to treat the underlying hypotensive condition. Conventionally, the HR measurements are compared 1006 to a threshold value (Z), that may be preset, for example, by the treating physician in order to detect an incidence of hypotension. Based on this comparison, which may be manifested by an algorithm contained in the therapeutic device (e.g., pacemaker or drug infusion pump), for example, a decision or directive 1008 may be made to deliver therapy 1010 if the HR falls below the threshold value (Z). If the HR exceeds the threshold value (Z), a decision or directive 1008 may be made to not deliver therapy, but rather to continue sampling HR measurements 1004.

However, because hypotension or inadequate tissue perfusion may manifest in a patient without a drop in HR, it is beneficial to measure 1002 one or more indicia (X) of hypotension or inadequate tissue perfusion. The one or more indicia (X) may be compared 1012 to a threshold value (Y), and the comparison 1012 may be made by an algorithm executed by the therapeutic device (e.g., pacemaker or drug infusion pump). Based on the comparison 1012, a decision or directive 1014 may be made to deliver therapy 1010 if the indicia (X) falls below the threshold value (Y). If the indicia (X) exceeds the threshold value (Y), a decision or directive 1014 is made to not deliver therapy, but rather to continue taking measurements 1002 of the indicia (X).

The other indicia (X) may comprise, for example, peripheral vascular blood pressure, intracardiac blood pressure, vascular blood flow or tissue perfusion. Any one or a combination of these indicia (X) may be measured in addition to or as a substitute for heart rate as measured by ECG or electrogram. The indicia may be measured by a separate device or by incorporating measurement capabilities in the therapeutic device. The interpretation, analysis and decision making functions may be carried out by an algorithm executed by suitable electronics in the therapeutic device.

The following detailed description starts with a description of exemplary methods to measure such indicia (X), followed by a description of exemplary measurement devices for measuring the associated indicia (X).

Description of Vascular and Cardiac Pressure Sensing Methods

One of the alternative indicia (X) may comprise, without limitation, vascular or cardiac blood pressure. An example of a pressure sensing device (PSD) 10 for measuring peripheral vascular blood pressure is described with reference to FIGS. 2, 3 and 4. An example of pressure sensing device 400 for measuring intracardiac blood pressure is described with reference to FIGS. 9 and 10. Alternative pressure measuring devices may also be employed, such as an intravascular stent or a vascular cuff with pressure measurement capabilities.

In this method, heart rate data obtained by ECG and/or electrogram may be simultaneously sensed and interpreted as pressure sensor data obtained by a pressure measurement device (e.g., device 10 or 400) to measure pressure in an artery or within the heart. The therapeutic device (e.g., a pacemaker or drug infusion pump) may evaluate the pressure sensed by the pressure measurement device on an ongoing basis, and may create a baseline or reference pressure that is the average of the pressures measured over a designated time period (e.g., 30 seconds). If the current pressure has dropped more than a predesignated amount below the reference pressure, the therapeutic device begins to deliver stimuli (e.g., electrical pulse series from a pacemaker or a bolus of drug from an infusion pump) to the heart to increase heart rate by a predetermined (programmable) amount. If the pressure does not return to within a predesignated range of the original reference value, the therapeutic device delivers further stimuli to increase heart rate. During the delivery of therapeutic stimulus, the pressure measurement device may periodically sample blood pressure and the therapeutic device may re-evaluate the pressure relative to the reference pressure. If pressure has returned to within an acceptable range of the reference pressure, the therapeutic device may begin a sequence whereby the stimulus is decreased and heart rate is gradually returned to a normal value. If the heart rate reaches a preset upper limit, stimulus delivery may be terminated, even if the measured pressure is below the acceptable target range.

Those skilled in the art will recognize that the reference pressure may or may not be adjusted for barometric pressure variations. The use of a reference pressure without barometric correction (as opposed to a control algorithm that employs an absolute pressure) obviates the need to employ a barometric pressure reference for correction of the intravascular or endocardial pressure measurements. This is valuable in that the need for a barometric pressure monitor adds complexity and cost to the system and may also require patient compliance, depending on how the barometric correction were implemented.

Description of Vascular Flow Sensing Method

One of the alternative indicia (X) may comprise, without limitation, vascular or cardiac blood flow. An example of a flow sensing device (FSD) 210 for measuring peripheral vascular blood flow is described with reference to FIGS. 5 and 6. Alternative devices for measuring blood flow may also be employed.

With blood flow measurements, the functional control of the stimulus delivery from the therapeutic device may be the same or similar as described with regard to blood pressure measurements. In other words, the delivery of stimulus may be triggered, maintained and/or shut-off using pre-programmed thresholds and ranges of blood flow similar to that which has been described previously for blood pressure.

With the flow sensing device, it may be beneficial for noise reduction purposes that the flow signal be integrated over a programmable number of complete cardiac cycles (e.g., 2 or 3 cycles). The integrated signal, referred to herein as the current flow value (CFV), may be compared to a baseline value comprising a running average of CFVs occurring over a programmed period of time. For example, CFVs that fall within a time interval (e.g., 30 second to 10 minute) prior to the current measurement may be used to create a baseline value of flow. The computed baseline value may serve as a reference value and current CFV may be compared to the reference value in a manner as described previously to detect changes in flow indicative of a need to modify heart rate with the therapeutic device.

Description of Tissue Perfusion Method

One of the alternative indicia (X) may comprise, without limitation, tissue perfusion. An example of a tissue perfusion monitor 310 (TPM) is described with reference to FIGS. 7 and 8. Alternative tissue perfusion measurement devices may also be utilized.

With tissue perfusion measurements, the functional control of the stimulus delivery from the therapeutic device may be the same or similar as described with regard to blood pressure measurements. In other words, the delivery of stimulus may be triggered, maintained and/or shut-off using pre-programmed thresholds and ranges of tissue perfusion similar to that which has been described previously for blood pressure.

A reference value for tissue perfusion may be obtained over a programmable period of time (e.g., 30 seconds to 10 minutes) to compute a running average. The computed running average, which may be periodically update, may serve as a reference value and current perfusion measurements may be compared to the reference value in a manner as described previously to detect changes in tissue perfusion indicative of a need to modify heart rate with the therapeutic device.

Description of Vascular Pressure Sensing Device

Figure 2:
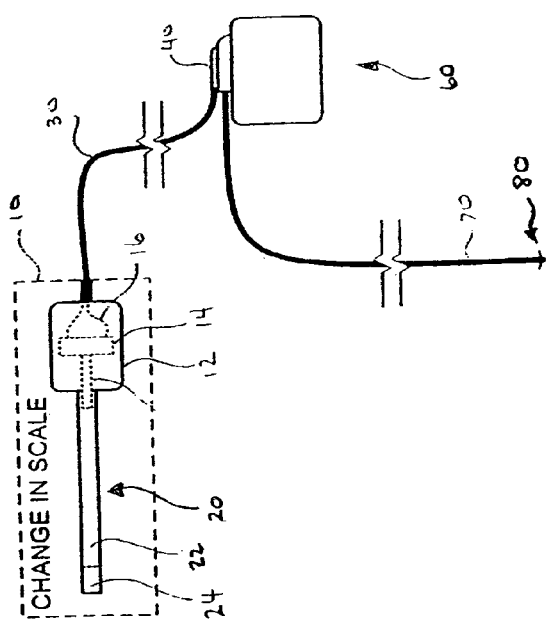
FIG. 2 is a schematic illustration of a system including an implantable pressure sensing device and a pacemaker.

With reference to FIG. 2, an implantable pressure sensing device (PSD) 10 and an implantable therapeutic device (ITD) 60 are shown. By way of example, not limitation, the ITD 60 is shown in the form of a pacemaker. The ITD 60 may comprise other therapeutic devices that increase heart rate, such as a drug infusion pump or a pacemaker. The following disclosure is given with specific reference to a pacemaker, but is understood to be equally applicable to other ITDs.

The PSD 10 is connected to the pacemaker 60 by an electrical lead 30. PSD 10 measures blood pressure and generates an electrical pressure signal which is transmitted in analog or digital form to the pacemaker 60 via lead 30. The lead 30 is preferably flexible, and may be similar to conventional pacing leads. A releasable connector 40 may be provided on the pacemaker 60 to facilitate easy connection and disconnection of the lead 30. This provides the physician with flexibility during placement of the lead 30 and PSD 10 as well as replacement of the PSD 10 at a later time should it fail or when the battery depletes.

The pacemaker 60 may otherwise be substantially conventional, with the exception of suitable signal processing electronics to receive and analyze (e.g., by a suitable algorithm) the pressure signal generated by the PSD 10. The pacemaker 60 may utilize a conventional endocardial lead 70 with a distal endocardial electrode 80 (as shown) to deliver the desired therapeutic electrical stimulus. Alternatively, subcutaneous (i.e., non-endocardial) electrodes may be used, such as those described in U.S. Patent Application Publication No. 2002/0107559 to Sanders et al., assigned to Cameron Health, the entire disclosure of which is incorporated herein by reference.

The PSD 10 includes a hermetically sealed housing 12 containing a pressure transducer 14 that converts fluidic pressure measurements or signals into electrical signals. The transducer 14 may be directly coupled by a plurality of wires 16 to lead 30 which transmits the electrical signals to the pacemaker 60, which provides the necessary signal processing and power supply functions. Alternatively, as seen in FIG. 2, the PSD 10 may provide these functions by containing within housing 12 an electronics module 13 and battery 15 for signal processing and power functions, respectively. These features are described in more detail in U.S. Pat. No. 6,033,366, to Brockway et al., the entire disclosure of which is incorporated herein by reference.

The PSD 10 also includes a pressure transmission catheter 20. The PTC 20 has a proximal end connected to the housing 12 and a distal end sized for insertion into a vascular lumen. The PTC 20 also includes a lumen in fluid communication with the pressure transducer contained in the housing 12. The lumen of the PTC 20 may be filled with a viscous fluid 22, with a distally disposed barrier 24 (e.g., gel plug or ePTFE membrane) that readily transmits pressure signals, but otherwise retains the fluid in the lumen of the PTC 20. Further aspects of the PTC 20 are disclosed in U.S. Pat. No. 4,846,191 to Brockway et al., the entire disclosure of which is incorporated herein by reference.

A significant benefit of the PTC 20 for measurement of pressure in a vascular lumen is that the size of the PTC 20 may be quite small. For example, the PTC 20 may be approximately 0.5 mm–1.5 mm diameter, which is substantially smaller than the 3.5 mm diameter pressure-sensing catheter used on the Chronicle™ device. In addition to a much smaller diameter, the portion of the PTC 20 that is inserted into the artery to assure a stable placement and obtain accurate pressure measurements is only about 5 mm to 10 mm, thus allowing the PTC 20 to be relatively short. One benefit of small size is that there is a much lower surface area of the sensor exposed to the blood. The smaller the surface area (all other factors such as material properties being equal) the lesser the risk of thrombo-embolism. A further benefit of smaller size is that the risk of hematoma is reduced (a small puncture in the vessel wall is more likely to seal tightly than is a larger hole). The smaller and lighter PSD 10 is more easily inserted (a small introducer can be used that results in significantly less bleeding during insertion and the need for extended application of pressure to stop bleed after introduction is greatly reduced), and is less likely to damage the endothelial surface (because lower mass and size is less likely to cause trauma if it bumps into the vessel wall as a result of blood flow eddies and changes in patient posture).

The PSD 10 and/or the pacemaker 60 may optionally include ECG electrodes for measuring heart rate and other electrophysiological parameters associated with cardiac function. For example, electrodes may be incorporated on the housing of the pacemaker 60, on the electrode lead 70 of the pacemaker 60, on the interconnect lead 30 between the PSD 10 and pacemaker 60, on the housing 12 of the PSD 10, and/or on the PTC 20 of the PSD 10. Such ECG electrodes may be electrically coupled to the signal processing circuitry of the pacemaker 60.

Figure 3:
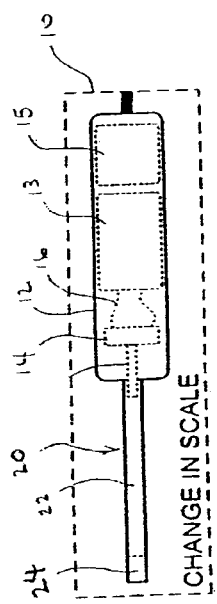
FIG. 3 is a schematic illustration of an alternative implantable pressure sensing device.

With reference to FIG. 3, the PSD 10 and the pacemaker 60 are shown implanted in a patient 100. The pacemaker 60 may be implanted in any of a number of conventional manners, such as with the lead 70 extending endocardially through the superior vena cava 112, through the right atrium 114, with the electrode 80 residing in the right ventricle 116 as shown. Alternatively, the electrode may reside in the right atrium 114, the coronary sinus, etc. As mentioned before, non-endocardial electrode placement may also be used, such as subcutaneous placement.

The PSD 10 is implanted in the patient 100 with at least the distal end of the PTC 20 disposed in a vascular lumen, such as the subclavian artery 1118, while the housing 12 of the PSD 10 remains outside the subject vascular lumen. The relatively small diameter and short length of the PTC 20 has minimal impact on blood flow. Arterial placement of the PTC 20 may be preferred over venous placement since the superior vena cava 112 already contains lead 70, and additional obstructions may compromise blood flow.

Although the PTC 20 is shown disposed in the subclavian artery 118, those skilled in the art will recognize that other non-endocardial or peripheral vascular sites are also possible, such as the pulmonary artery, brachial artery or the femoral artery, for example. Furthermore, although the PSD 10 provides significant benefit for detecting hypotension when used to measure pressures in non-endocardial sites (e.g., peripheral artery), the PSD 10 may also be effectively used in this application for measuring endocardial pressure in any chamber of the heart 110. An example of this latter approach is described with reference to FIGS. 9 and 10.

To determine if the patient is experiencing hypotension, the signal processing circuitry of the pacemaker 60 evaluates the pressure signal generated by the PSD 10, either alone or in combination with an ECG signal. Signal processing circuitry known to those skilled in the art may be used to detect hypotension as a trigger for stimulus. A function (e.g., algorithm) for both the pressure and ECG signals may be used to indicate the likelihood that a hypotensive episode requiring stimulus is occurring in the patient 100.

Description of Vascular Flow Sensing Device

Figure 4:
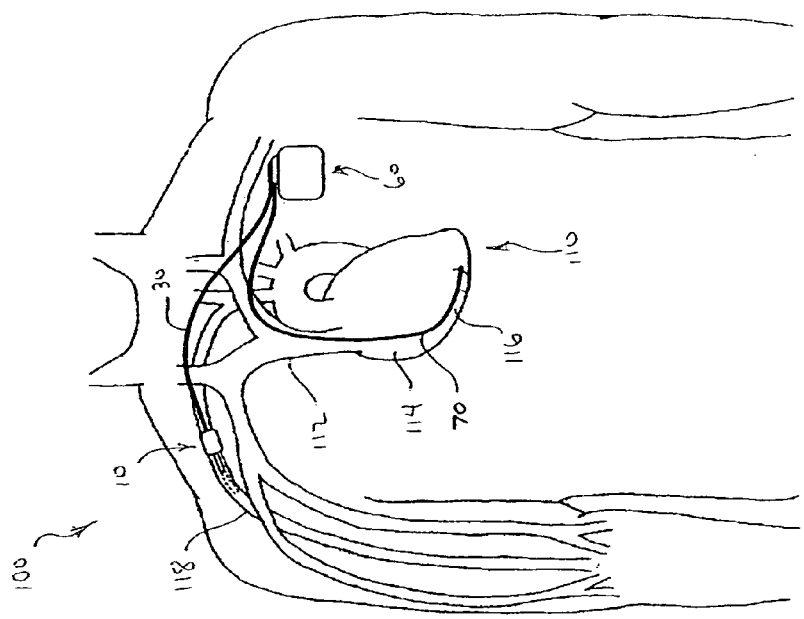
FIG. 4 is a schematic illustration of a pressure sensing device and a pacemaker shown implanted in a patient.

With reference to FIGS. 5 and 6, a flow sensing device (FSD) 200 may be used in place of the PSD 10 described with reference to FIGS. 2, 3 and 4. In this alternative embodiment, the FSD 200 measures blood flow rate and generates an electrical flow signal which is transmitted in analog or digital form to the pacemaker 60 via lead 30. The flow measurement signal is indicative of inadequate tissue perfusion and the need to deliver stimulus with pacemaker 60.

FSD 200 includes a transducer cuff assembly 210 and an electronics assembly 220. Cuff assembly 210 includes a housing 212 sized and shaped to fit around a blood vessel, such as subclavian artery 118. Cuff housing 212 may be formed of a flexible polymer or rubber such as silicone rubber. Alternatively, cuff housing 212 may be formed of a more rigid moldable biocompatible polymer, for example, and may available in different sizes to accommodate vessels of different diameters. An example of a suitable cuff design is disclosed in U.S. Patent Application Publication No. 2002/0072731 to Doten et al., the entire disclosure of which is incorporated by reference.

A plurality of transducers 214 are disposed in the housing 212 at diametrically opposite positions so as to direct ultrasound at the vessel at a 45 degree angle, for example, to facilitate flow measurement within the vascular lumen. The transducers 214 may be ultrasonic transducers, for example, and blood flow may be measured by continuous wave Doppler, pulsed Doppler, or transit time techniques, for example. Other flow measurement techniques such as thermal dilution may be used as well. The transducers 214 of the cuff assembly 210 may be connected to a separate electronics assembly 220 by lead 218. Electronics assembly 220 includes a hermetically sealed housing 222 containing a suitable signal processing circuit 224 and battery power source 226. An example of a suitable transducer arrangement and electronics assembly is described in U.S. Pat. No. 5,865,749 to Doten et al., the entire disclosure of which is incorporated herein by reference.

It may be beneficial to employ a pulsed Doppler technique to allow for flow to be measured using very low power by positioning a single Doppler flow crystal on the outer surface of the artery or vein. Such Doppler flow "cuffs" are available commercially from Crystal Biotech (Hopkinton, Mass.) and by Prof. Craig Hartley (Baylor School of Medicine, Houston, Tex.). Such a cuff could be located on many different arteries and veins located under the skin or within the body, but the subclavian artery or vein would be a good choice. Optionally, the Doppler flow crystal may be incorporated into the pacing lead 70, or into a flexible lead designed specifically for that purpose, such as those commercially available from Millar Instruments (Houston, Tex.). Such a lead may plug directly into the header of the pacemaker via a connector similar to an IS1 connector.

Description of Tissue Perfusion Monitor

Figure 8:
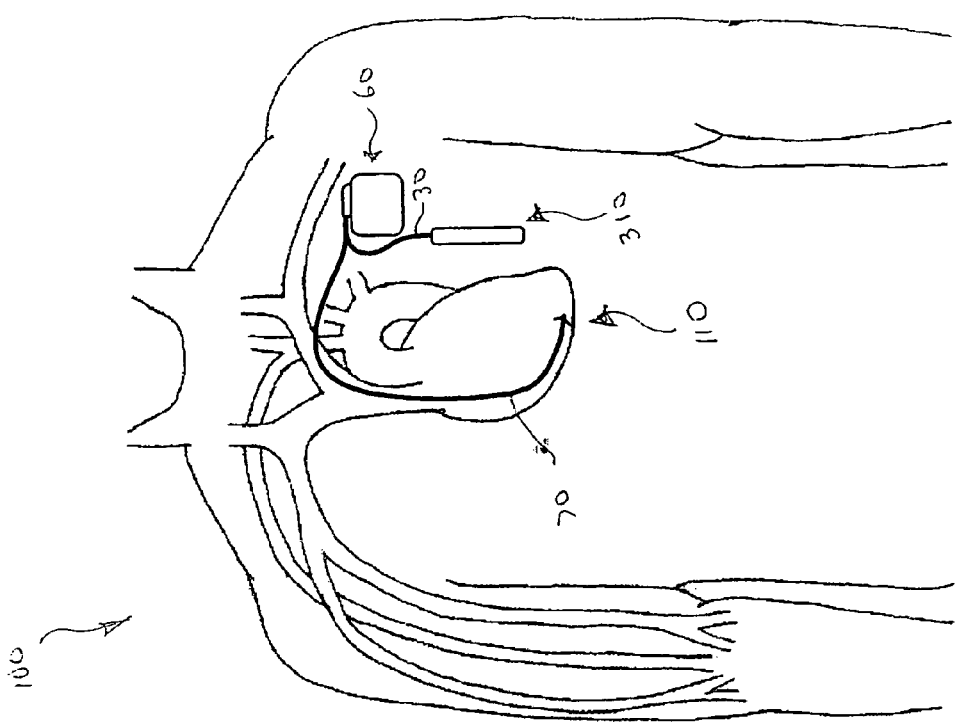
FIG. 8 is a schematic illustration of a tissue perfusion monitor and a pacemaker shown implanted in a patient.
Figure 7:
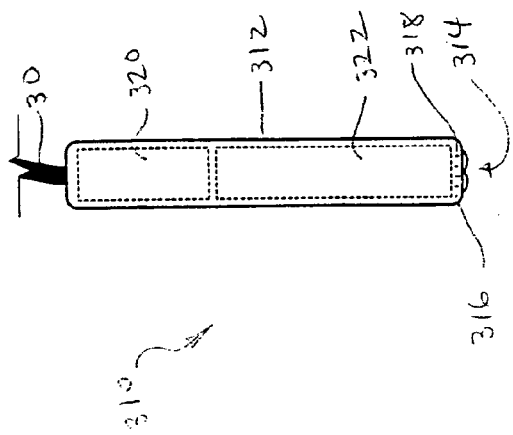
FIG. 7 is a schematic illustration of a tissue perfusion monitor that may be used in place of the pressure sensing device.

With reference to FIGS. 7 and 8, a tissue perfusion monitor (TPM) 310 may be used in place of the PSD 10 described previously. In this alternative embodiment, the TPM 310 measures blood perfusion in bodily tissue and generates a blood perfusion signal which is transmitted in analog or digital form to the pacemaker 60 via lead 30. The degree of tissue perfusion as measured by TPM 310 may be used in a manner similar to how hemodynamic measurements can be used to provide a more effective therapy, either alone or in combination with other information such as ECG and pressure.

The TPM 310 may utilize, for example, laser Doppler techniques to measure blood perfusion in tissue. The laser Doppler flow sensor reflects laser light off bodily tissue and the return signal is indicative of the movement of blood through capillaries contained in the tissue. The sensor may be incorporated into the therapeutic device 60 (e.g., implantable housing or electrode lead) or may comprise a separate device 310 as shown. The sensor may be located in an area where changes in tissue perfusion would not be induced by everyday activities such as pressure applied to an area of the skin. In order to maintain current drain of the sensor at a sufficient low level, it may be beneficial to duty cycle the sensor such that it takes measurements at regular intervals, between which the current drain of the electronics is reduced to a minimum.

As seen in FIG. 7, the TPM 310 includes a hermetically sealed housing 312 containing a source of coherent light (e.g., laser) 316 and one or more photodetectors 318 with associated collecting lenses 314 which interface with the tissue to be monitored. For purposes of the clinical applications discussed herein, any well vascularized tissue may be monitored at a convenient in-vivo site such as adjacent the pacemaker 60 as shown in FIG. 8. The photodetectors 318 are connected to suitable signal processing circuitry 322 powered by battery 320. Examples of suitable laser Doppler componentry may be found in U.S. Pat. No. 6,259,936 to Boggett et al. and European Patent Application No. 0282210A1 to Fujii.

A benefit of the TPM 310 is that it does not require insertion into an artery or cardiac chamber. Another benefit is that the TPM 310 may be incorporated as an integral part of the pacemaker 60, with the lenses extending through the housing and the light emitter/detector and electronics disposed inside the housing, thus eliminating the need for additional leads. This would have particular benefit for use with subcutaneously implanted defibrillators, since it is an objective of such devices to eliminate the use of any leads.

Description of Intracardiac Pressure Sensing Device

With reference to FIGS. 9 and 10, a combined pressure sensing and electrode device (PSED) 400 is shown. The PSED 400 generally includes a PSD 10 as described previously, in addition to an anchoring electrode 410, which facilitates both as a stimulus electrode for pacing purposes, and as an anchor to hold the PSD 10 to the atrial septal wall 115, for example, with the PTC 20 extending across the septal wall 115 and into the left atrium 117. The PSED 400 in conjunction with the pacemaker 60 allows for both the delivery of therapeutic stimulus (e.g., pacing) via electrode 410 to the intra-atrial septum 115 and the measurement of pressure in the left atrium 117 for feedback and triggering purposes, for example.

Those skilled in the art will recognize that the PSED 400 may be positioned such that the PSD 10 resides inside or outside the heart and the distal end of the PTC 20 resides in any desired chamber of the heart 110. For example, the PTC 20 may be positioned across the left ventricular lateral wall such that the distal end of the PTC 20 is disposed in the left ventricle and the PSD 10 is mounted to the epicardial surface of the left ventricular lateral wall. As an alternative, the PTC 20 may be positioned across the right ventricular lateral wall such that the distal end of the PTC 20 is disposed in the right ventricle and the PSD 10 is mounted to the epicardial surface of the right ventricular lateral wall. As a further alternative, the PTC 20 may be positioned across the atrial septal wall or the ventricular septal wall such that the distal end of the PTC 20 is disposed in the left or right atrium or the left or right ventricle, respectively, with the PSD mounted to the opposite side of the septal wall.

The PSED 400 may be implanted as shown in FIG. 10 by using conventional atrial pacing procedure to position the PSED 400 in the right atrium 114. The PTC 20 may be disposed across the atrial septal wall 115 by using transseptal approach similar to that which is used to deliver electrophysiology catheters in the left atrium 1117. For example, using fluoroscopic visualization, a guide wire or needle may be used to puncture the septal wall 115, and radiopaque dye may be injected to confirm complete puncture and placement. A dilator and sheath may be advanced over the guide wire to access the left atrium 117. The PSED 400 may then be advanced through the sheath and/or along the guide wire (with the use of a guide wire lumen on the side of the PSED 400), until the PTC 20 extends across the punctured septum 115. The PSED 400 may then be rotated (for a corkscrew-type anchor) or pushed (for a barb-type anchor) to secure the PSED 400 to the septal wall 115.

In this alternative embodiment, the PSED 400 measures blood pressure in the left atrium and generates an electrical pressure signal which is transmitted in analog or digital form to the pacemaker 60 via lead 30.

Figure 11:
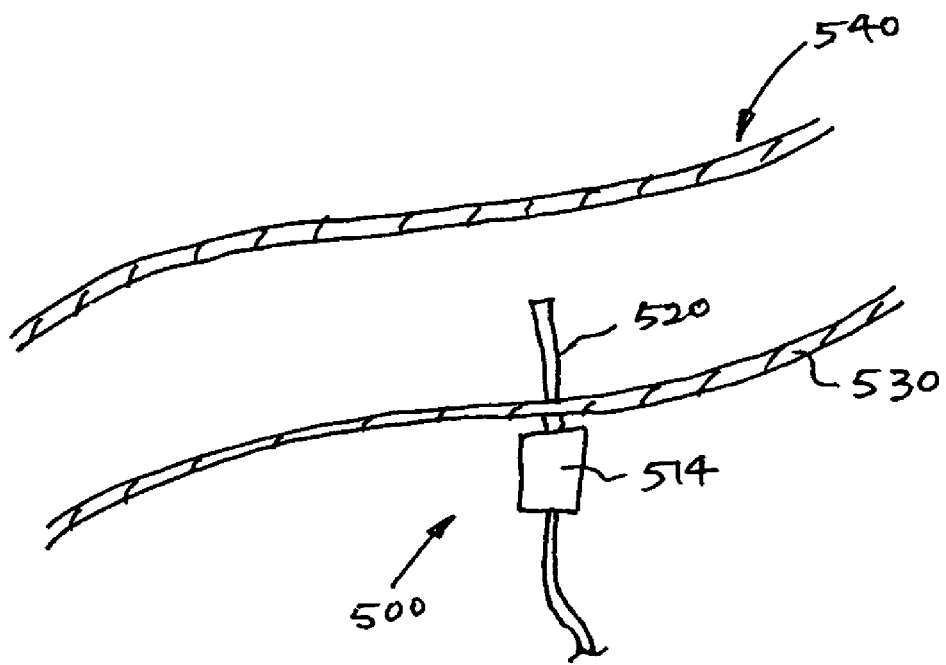
FIG. 11 is a schematic illustration of a pressure sensing device with an anchoring electrode shown implanted across a wall of a patient's blood vessel.

From the foregoing, it will be apparent to those skilled in the art that the present invention provides, in exemplary no-limiting embodiments, implantable devices that measure vascular pressure, vascular blood flow, tissue perfusion, and/or intracardial pressure, and provide feedback directly to a therapeutic device to improve detection and treatment of inadequate tissue perfusion. For instance, FIG. 11 shows a sensor 500 which includes a transducer 514 and a catheter 520, wherein the catheter 520 extends through a wall 530 and inside a lumen of the blood vessel 540 and the transducer 514 resides outside the blood vessel 540. Further, those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A medical method for treating a patient, comprising:
    detecting heart rate as an indicator of inadequate tissue perfusion;
    detecting at least one other indicia of inadequate tissue perfusion;
    delivering a stimulus to increase tissue perfusion as a function of both heart rate and the at least one other indicia; and
    providing a therapeutic device for delivering the stimulus to increase tissue perfusion;
    wherein the step of delivering the stimulus comprises delivering a stimulus to increase heart rate.

2. A medical method as in claim 1, wherein the step of providing a therapeutic device comprises providing a pacemaker, and wherein the step of delivering the stimulus to increase heart rate comprises delivering electrical impulses to the patient's heart.

3. A medical method as in claim 1, wherein the step of providing a therapeutic device comprises providing an infusion pump, and wherein the step of delivering the stimulus to increase heart rate comprises delivering a bolus of a drug.

4. A medical method as in claim 1, wherein the step of detecting at least one other indicia of inadequate tissue perfusion comprises detecting blood pressure.

5. A medical method as in claim 4, wherein the step of detecting blood pressure comprises detecting vascular blood pressure.

6. A medical method as in claim 4, wherein the step of detecting blood pressure comprises detecting intracardiac blood pressure.

7. A medical method as in claim 1, wherein the step of detecting at least one other indicia of inadequate tissue perfusion comprises detecting blood flow.

8. A medical method as in claim 7, wherein the step of detecting blood flow comprises detecting vascular blood flow.

9. A medical method as in claim 1, wherein the step of detecting at least one other indicia of inadequate tissue perfusion comprises detecting blood perfusion in tissue.

10. A medical method as in claim 9, wherein the step of detecting blood perfusion in tissue comprises detecting blood perfusion in tissue in the patient's upper body.

11. A medical method as in claim 9, wherein the step of detecting blood perfusion in tissue comprises detecting blood perfusion in tissue in the patient's chest.

12. A medical method as in claim 9, wherein the step of detecting blood perfusion in tissue comprises detecting blood perfusion in tissue in the patient's head or neck.

* * * * *